United States Patent
McCoy

(10) Patent No.: US 7,458,267 B2
(45) Date of Patent: Dec. 2, 2008

(54) ACOUSTIC EMISSION INSPECTION OF COILED TUBING

(75) Inventor: Terry H. McCoy, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 10/990,923

(22) Filed: Nov. 17, 2004

(65) Prior Publication Data
US 2006/0101914 A1    May 18, 2006

(51) Int. Cl.
G01N 29/00    (2006.01)
E21B 17/20    (2006.01)

(52) U.S. Cl. .............................. 73/587; 73/592; 73/622; 73/644; 166/384

(58) Field of Classification Search .................. 73/622, 73/597, 587, 593, 592, 599, 602, 644, 801, 73/812, 813; 166/384, 308, 385
See application file for complete search history.

(56) References Cited

U.S. PATENT DOCUMENTS

| | | | | |
|---|---|---|---|---|
| 4,332,161 A * | 6/1982 | Kakino | .......................... | 73/104 |
| 4,448,062 A * | 5/1984 | Peterson et al. | ................. | 73/86 |
| 4,499,769 A * | 2/1985 | Conway | ...................... | 73/587 |
| 4,658,245 A | 4/1987 | Dye et al. | | |
| 4,667,095 A * | 5/1987 | Hatanaka et al. | ............. | 250/226 |
| 5,303,592 A * | 4/1994 | Livingston | .................... | 73/622 |
| 5,526,689 A * | 6/1996 | Coulter et al. | ................. | 73/592 |
| 5,767,671 A | 6/1998 | McCoy et al. | | |
| 5,803,168 A | 9/1998 | Lormand et al. | | |
| 5,826,654 A * | 10/1998 | Adnan et al. | ............ | 166/250.01 |
| 5,914,596 A * | 6/1999 | Weinbaum | .................... | 324/228 |
| 6,321,596 B1 * | 11/2001 | Newman | .................. | 73/152.45 |
| 6,354,146 B1 * | 3/2002 | Birchak et al. | .............. | 73/61.79 |
| 6,457,534 B1 * | 10/2002 | Rolovic et al. | ............... | 166/381 |
| 6,719,043 B2 | 4/2004 | Austbo et al. | | |
| 6,732,545 B2 | 5/2004 | Cadet et al. | | |

(Continued)

FOREIGN PATENT DOCUMENTS

WO    WO 2004/090528 A1    10/2004

OTHER PUBLICATIONS

Foreign communication from related counter part application dated Feb. 2, 2006.

(Continued)

*Primary Examiner*—Hezron E. Williams
*Assistant Examiner*—Jacques M. Saint-Surin
(74) *Attorney, Agent, or Firm*—John W. Wustenberg; Baker Botts, L.L.P.

(57) ABSTRACT

A method for testing tubing having the following steps: plastically deforming the tubing with a tubing handling system, the tubing handling system having a reel, a gooseneck and an injector; sensing with at least one sensor acoustic emissions emitted by the tubing during the deforming; and processing acoustic emission signals sensed from the tubing during the deforming. A system for testing a coiled tubing, the system having: a tubing handling system, the tubing handling system having a reel, a gooseneck and an injector; at least one acoustic emission sensor mounted on the tubing handling system and in direct contact with the tubing; and an acoustic emission signal processor in signal transmission communication with the at least one acoustic emission sensor.

28 Claims, 4 Drawing Sheets

U.S. PATENT DOCUMENTS

| | | | | |
|---|---|---|---|---|
| 6,748,808 | B2 * | 6/2004 | Lam et al. | 73/622 |
| 6,782,751 | B2 * | 8/2004 | Linares et al. | 73/622 |
| 6,862,099 | B2 * | 3/2005 | Lam et al. | 356/635 |
| 7,028,543 | B2 * | 4/2006 | Hardage et al. | 73/152.01 |
| 7,080,557 | B2 * | 7/2006 | Adnan | 73/622 |

OTHER PUBLICATIONS

Paper entitled "Acoustic Emission Techniques in Nondestructive Evaluation," Part III, pp. 181-208.

Web page www.pacndt.com, "Acoustic Emission Technology," Physical Acoustics Corporation.

Web page www.pacndt.com, "Leak Monitoring and Detection Systems," Physical Acoustics Corporation.

Web page www.pacndt.com, "Complete Acoustic Emission Product Line," Physical Acoustics Corporation.

Web page www.pacndt.com, "Knowledge Based Systems," Physical Acoustics Corporation.

Web page www.pacndt.com, "Rolling Sensor (Dry-Contact)," Physical Acoustics Corporation.

Web page www.pacndt.com, "Acoustic Emission Testing and Analysis Software," Physical Acoustics Corporation.

Web page www.pacndt.com, "Multichannel Acoustic Emission Systems," Physical Acoustics Corporation.

Web page www.pacndt.com, "Acoustic Emission Amplifiers," Physical Acoustics Corporation.

Web page www.pacndt.com, "Acoustic Emission Measurment Technologies," Physical Acoustics Corporation.

"Standard Practice for Acoustic Emission Monitoring of Structures During Controlled Stimulation," ASTM Internation, pp. 1-5.

"Acoustic Emission Techniques in Nondestructive Evaluation," Part III, pp. 181-208, 1997.

www.pacndt.com, "Acoustic Emission Technology," Physical Acoustics Corporation, Sep. 17, 2004.

www.pacndt.com, "Leak Monitoring and Detection Systems," Physical Acoustics Corporation, Sep. 15, 2004.

www.pacndt.com, "Complete Acoustic Emission Product Line," Physical Acoustics Corporation, Sep. 14, 2004.

www.pacndt.com, "Knowledge Based Systems," Physical Acoustics Corporation, Sep. 15, 2004.

www.pacndt.com, "Rolling Sensor (Dry-Contact)," Physical Acoustics Corporation, Sep. 14, 2004.

www.pacndt.com, "Acoustic Emission Testing and Analysis Software," Physical Acoustics Corporation, Sep. 15, 2004.

www.pacndt.com, "Multichannel Acoustic Emission Systems," Physical Acoustics Corporation, Sep. 15, 2004.

www.pacndt.com, "Acoustic Emission Amplifiers," Physical Acoustics Corporation, Sep. 15, 2004.

www.pacndt.com, "Acoustic Emission Measurment Technologies," Physical Acoustics Corporation, Sep. 14, 2004.

"Standard Practice for Acoustic Emission Monitoring of Structures During Controlled Stimulation," ASTM Internation, pp. 1-5, Aug. 5, 2004.

* cited by examiner

ACOUSTIC EMISSION INSPECTION OF COILED TUBING

BACKGROUND

This invention relates to coiled tubing systems used in wells, such as oil or gas wells. In particular, this invention relates to methods and apparatuses for determining the useful life and integrity of coiled tubing strings.

Coiled tubing may be introduced into an oil or gas well bore through wellhead control equipment to perform various tasks during the exploration, drilling, production, and workover of the well. Coiled tubing may be used, for example, to inject gas or other fluids into the well bore, to inflate or activate bridges and packers, to transport tools downhole such as logging tools, to perform remedial cementing and clean-out operations in the bore, to deliver drilling tools downhole, for electric wireline logging and perforating, drilling, wellbore cleanout, fishing, setting and retrieving tools, for displacing fluids, and for transmitting hydraulic power into the well. The flexible, lightweight nature of coiled tubing makes it particularly useful in deviated well bores.

Coiled tubing generally includes a small diameter cylindrical tubing made of metal or composite that has a relatively thin cross sectional thickness (e.g., from 0.067 to 0.203 inches (1.70-5.16 mm)). The continuous length of coiled tubing is a flexible product made from a steel strip. The strip is progressively formed into a tubular shape and a longitudinal seam weld is made by electric resistance welding (ERW) techniques. The product is typically several thousand feet long and is wound on a reel.

Conventional handling systems for coiled tubing can include a reel assembly, a gooseneck, and a tubing injector head. Reel assemblies may include a rotating reel for storing coiled tubing, a cradle for supporting the reel, a drive motor, and a rotary coupling. When the coiled tubing is introduced into a well bore, the tubing injector head draws the coiled tubing stored on the reel and injects the coiled tubing into a wellhead. The drive motor rotates the reel to pay out the coiled tubing and the gooseneck directs the coil tubing into the injector head. Often, fluids are pumped through the coiled tubing during operations. The rotary coupling provides an interface between the reel assembly and a fluid line from a pump.

During the injection process, coiled tubing is subjected to fatigue caused by "bending events" that may eventually lead to structural failure. At least three bending events may occur before newly manufactured coiled tubing even enters a well bore: unbending when the coiled tubing is first unspooled from the reel, bending when traveling over a gooseneck, and unbending upon entry into an injector. Bending the tubing creates severe flexural strains and plastic deformation of the tubing. For coiled tubing used in oil or gas wells, such plastic deformation can include strains typically within the range of about 0.01 to about 0.02, but can be higher depending on the coiled tubing size and bend radius utilized. Coiled tubing is also subjected to downhole stresses induced by friction between the coiled tubing and the well casing or well bore. Depending on the application, coiled tubing may also be subjected to internal and external pressure as fluids are pumped through the coiled tubing and/or as the coiled tubing is lowered to depths were hydrostatic fluid pressures are significant. Well bore environments may also be corrosive and subject to significant variations in temperature. An accumulation of bending events and other stresses can seriously undermine the integrity of coiled tubing.

To ensure that the coiled tubing does not fail during a wellbore operation, the coiled tubing is usually retired from service after only a few trips into a well bore. Software modeling may be used to estimate the fatigue life utilization of coiled tubing so as to get as much useful life out of the coiled tubing before it is retired. Modeling is used to determine when a coiled tubing should be taken out of service because of degradation brought about by the noted effects. Numerical models have been created to estimate how many cycles a particular type of coiled tubing can be used. Once an estimate has been determined, data is obtained when the coiled tubing is used so that the number of cycles of actual use can be known. However, this technique does not account for the specific condition of a particular coiled tubing or of all the environments in which it is used, other than possibly by way of some selected general adjustment factor (e.g., some factor assumed for a given corrosive environment).

Coiled tubing degradation is cumulative and ultimately leads to the point of catastrophic failure (complete breaking or severing) if the coiled tubing is used too long. Plasticity and fatigue models only estimate the actual condition of a particular coiled tubing string and must additionally include safety factors to insure that the coiled tubing string is retired from service before catastrophic failure occurs. However, premature retirement of the coiled tubing string results in economic losses. To avoid catastrophic failure, it is not uncommon for the coiled tubing to be removed from service at 50% of predicted life based on numerical model predictions. For example, if twenty-five 15,000 ft. coiled tubings are retired at 50% of their useful lives each year at a cost of $2/foot, the annual cost is $750,000. If the coiled tubings were not retired until 75% of useful life (i.e., a 50% increase over the foregoing example) had been expended, coiled tubing costs would be reduced (by $375,000 relative to the foregoing example) without increasing risk of catastrophic failure due to overextended use of the coiled tubing. Using the coiled tubing until nearly 100% of its useful life has been expended produces further savings.

SUMMARY

This invention relates to coil tubing systems. In particular, this invention relates to methods and apparatuses for determining useful life and integrity of coiled tubing strings.

According to one aspect of the invention, there is provided a method for testing tubing having the following steps: plastically deforming the tubing with a tubing handling system; sensing with at least one sensor acoustic emissions emitted by the tubing during the deforming; and processing acoustic emission signals sensed from the tubing during the deforming.

A further aspect of the invention provides a method for testing tubing having the following steps: plastically deforming the tubing with a tubing handling system, the tubing handling system having a reel, a gooseneck and an injector; sensing, with at least one rolling sensor in direct contact with the tubing, acoustic emissions emitted by the tubing during the deforming; and processing acoustic emission signals sensed from the tubing during the deforming, wherein the processing comprises amplifying, filtering and analyzing with knowledge-based software, the acoustic emission signals; and generating an alarm when the processing acoustic emission signals indicates that a region of the tubing containing a defect has insufficient strength to support a stress level about 60% or greater of the tensile strength of the tubing.

According to another aspect of the invention, there is provided a system for testing a coiled tubing, the system having:

a tubing handling system; at least one acoustic emission sensor mounted on the tubing handling system and in direct contact with the tubing; and an acoustic emission signal processor in signal transmission communication with the at least one acoustic emission sensor.

Still another aspect of the invention provides a system for testing a coiled tubing, the system having: a tubing handling system, the tubing handling system having a reel, a gooseneck and an injector, wherein the tubing handling system plastically deforms the tubing; at least one rolling acoustic emission sensor mounted on the tubing handling system and in direct contact with the tubing; an acoustic emission signal processor in signal communication with the at least one acoustic emission sensor, wherein the acoustic emission signal processor comprises an amplifier, a filter, and knowledge-based software; and an alarm in signal communication with the acoustic emission signal processor, wherein the alarm is activated when the acoustic emission signal processor indicates that a region of the tubing has insufficient strength to support a certain stress level.

The objects, features, and advantages of the present invention will be readily apparent to those skilled in the art upon a reading of the description of the preferred embodiments that follows.

BRIEF DESCRIPTION OF THE FIGURES

The present invention is better understood by reading the following description of non-limiting embodiments with reference to the attached drawings wherein like parts of each of the several figures are identified by the same referenced characters, and which are briefly described as follows.

It is to be noted, however, that the appended drawings illustrate only a few aspects of certain embodiments of this invention and are therefore not limiting of its scope, as the invention encompasses equally effective additional or equivalent embodiments.

DETAILED DESCRIPTION

This invention relates to coil tubing systems. In particular, this invention relates to methods and apparatuses for determining useful life and integrity of coiled tubing strings.

The tubing is acoustic emission tested while the tubing is deformed under stress in a coiled tubing handling system. An acoustic emission is a transient elastic wave generated by the rapid release of energy within the material of the tubing. Coil tubing made of metals, ceramics, and composites may be tested to identify failure points due to crack propagation, yielding, fatigue, corrosion and stress corrosion, creep, and fiber fracture or delamination.

Figure 1:
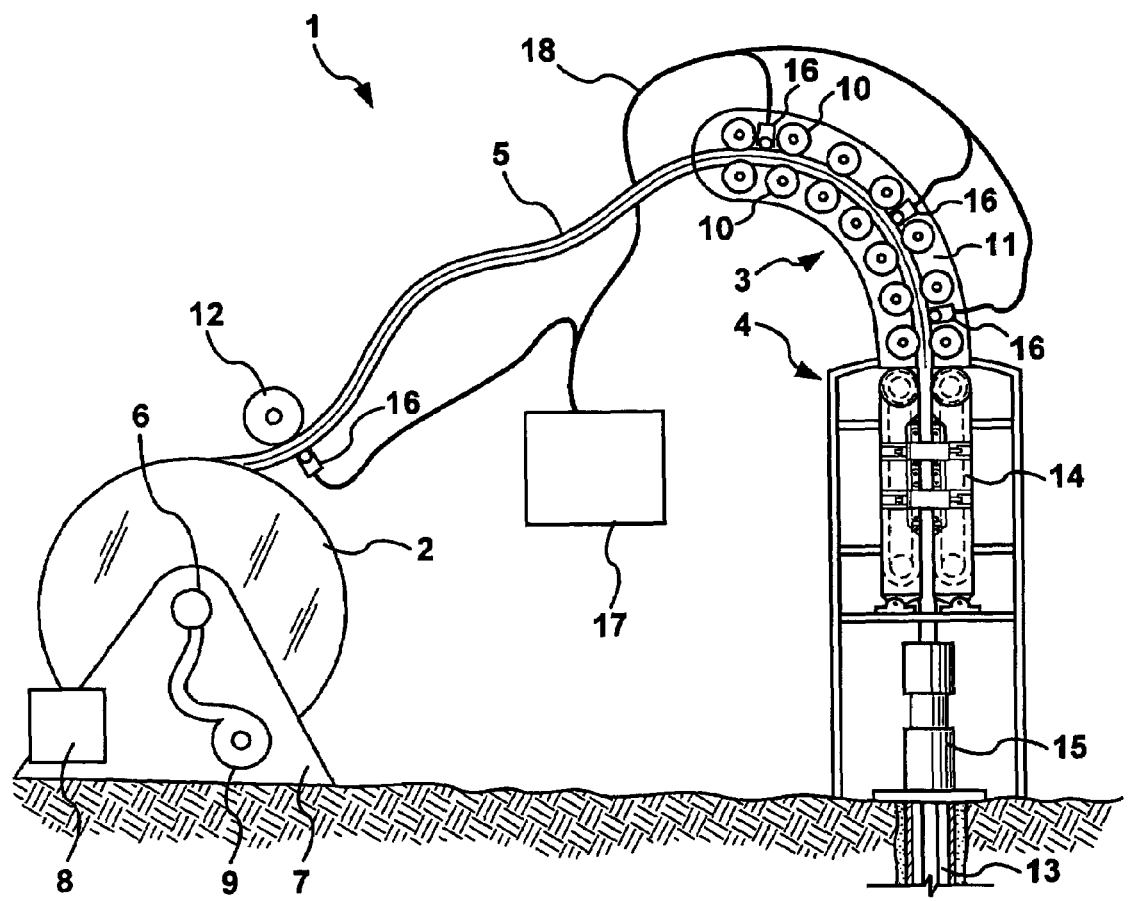
FIG. 1 is a cross-sectional, side view of a coil tubing handling system having a reel, a gooseneck, an injector, and acoustic emission sensors positioned at various locations in the system.

Referring to FIG. 1, a cross-sectional, side view is shown of a coiled tubing handling system 1. The system 1 has a reel 2, a gooseneck 3, and a tubing injector head 4. The tubing 5 extends from the reel 2, through the gooseneck 3 and into the injector head 4. The reel 2 rotates on an axle 6 and is supported by a cradle 7. A drive motor 8 is connected to the cradle 7 and is rotary coupled to the reel 2. Fluids are pumped through the coiled tubing 5 by a pump 9 that is fluidly connected to the tubing 5 through the reel 2. A rotary coupling (not shown) provides an interface between a fluid line from a pump 9 and the reel 2. A guide roller 12 is mounted to the cradle 7 adjacent to the reel 2. As the tubing unwinds from the reel 2, it is guided by the guide roller 12.

The gooseneck 3 is an arcuate structure for guiding the tubing into the injector head 4. The gooseneck 3 has an arcuate frame 11 that supports a series of opposing rollers 10. The rollers 10 are positioned on opposite sides of the tubing 5 to ensure that the tubing 5 follows a certain path through the gooseneck 3 toward the injector head 4.

The injector head 4 is aligned along the axis of the well bore and pushes/pulls the tubing in/out the well bore 13. The injector head 4 has a pair of oppositely positioned tracks 14. The tracks 14 each have a plurality of treaded paddles that grab or engage the tubing 5. Because the tracks 14 are positioned on opposite sides of the tubing 5, the tubing 5 is squeezed between the tracks 14. The tracks 14 are driven by an injector motor (not shown) that pushes or pulls the tubing 5.

When the coiled tubing 5 is introduced into a well bore 13, the tubing injector head 4 draws the coiled tubing 5 stored on the reel 2 and injects the coiled tubing 5 into a well head 15. The drive motor 8 rotates the reel 2 to pay out the coiled tubing 5 and the gooseneck 3 directs the coil tubing 5 into the injector head 4.

FIG. 1 further illustrates acoustic emission components that are used to monitor the actual structural integrity of the tubing 5. In particular, sensors 16 are positioned to be in contact with the tubing 5. The sensors 16 may be positioned at various locations in the system. For example, a sensor 16 may be positioned opposite the guide roller 12 to test the tubing as it bends past the guide roller 12. Sensors 16 may also be positioned in the gooseneck 3 between the rollers 10 to test the tubing 5 as the tubing 5 moves through the rollers 10. Depending on the configuration of the injector head 4, sensors may also be positioned therein or in any convenient place allowing direct contact of the sensor 16 with the tubing 5. The sensors may be strategically placed within the tubing handling system to be proximate to the portions of the tubing experiencing bending events as the tubing moves through the handling system. The sensors 16 transmit signals to a signal processor 17. Signal transmission from the sensors 16 to the signal processor 17 may be any means known to persons of skill in the art. By way of example, transmission cables 18 are illustrated.

One type of sensor 16 applicable for use with the present invention is a rolling sensor. The rolling sensor has a compliant tire that makes a good acoustic contact with the tubing for acoustic emission signal transfer from the tubing 5 to a receiver without the need for a couplant. The rolling sensor allows constant testing of the tubing as the tubing 5 is moved to and from the well bore 13. The rolling sensor may also be configured to move with irregularities in the tubing so as to maintain a constant pressure between the sensor and the tubing as irregularities in the tubing pass by the sensor. Depending on whether the tubing is made of metal or a composite, the sensor may accommodate wide bandwidths for frequency analysis. According to one embodiment of the invention, the sensor is capable of operating between temperatures of −45° C. to 100° C., and has a peak sensitivity of about 50 V/(m/s) responsive to surface waves (angle of incidence transverse or parallel to the face of the sensor). The sensor may also have a peak sensitivity of −74 V/(m/s) in response to plane waves (angle of incidence normal to face of sensor). The sensor may also operate within a frequency range of 200-1000 kHz. Suitable rolling sensors are available from Physical Acoustics Corporation of Princeton, N.J.

Figure 2:
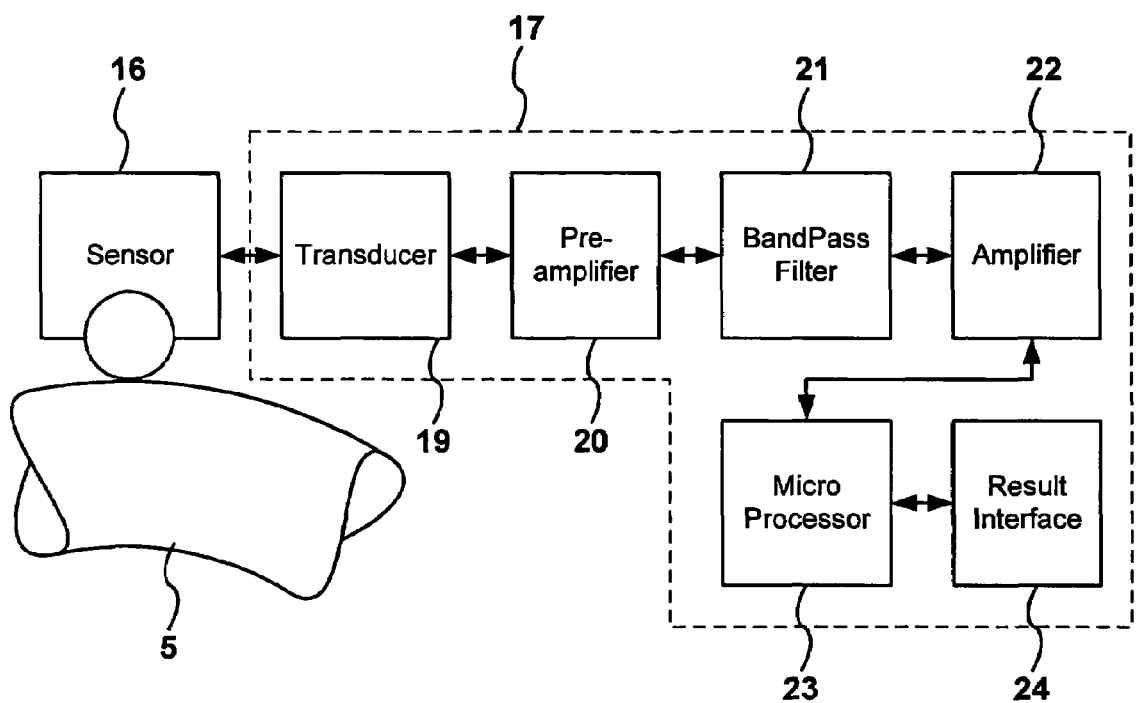
FIG. 2 is a block diagram illustrating component parts of a signal processor of the present invention.

Acoustic emission instrumentation for detection, measurement, recording and evaluation of signals is connected to the sensor 16. Referring to FIG. 2, components of a signal processor for use with the present invention are illustrated. The signal processor 17 may comprise a transducer 19, a preamplifier 20, a bandpass filter 21, an amplifier 22, a micro processor 23, and a result interface 24. Due to background noise captured by the sensors, the way the signals are gated, filtered, and interpreted may be optimized as known to persons of skill in the art. Because the output voltage of acoustic emission sensors is typically very small (<1 millivolt), a preamplifier 20 may be used to magnify the signal for analysis by a micro processor 23. Preamplifiers and/or postamplifiers may be used to manipulate the signal. Preamplifiers may be connected directly between an acoustic emission sensor and a postamplifier. Suitable pre- and post-amplifiers are available from Physical Acoustics Corporation of Princeton, N.J.

The micro processor 23 of the signal processor 17 may also comprise a multichannel system. Personal computer based multichannel systems may be local area network connected to provide additional multi-channel capacity. The micro processor 23 may also comprise knowledge-based analysis software that provides powerful and comprehensive analysis of the signals received from the sensors. Signal processing electronics may be used to extract features and capture the waveforms. The micro processor 23 may use parallel distributing processing instrumentation. Decision and feedback electronics may be used to analyze and correlate defects identified in the tubing 5. The software correlates the acoustic emission signal level and the status of the tubing 5 being tested. Suitable multichannel systems and acoustic emission software are available from Physical Acoustics Corporation of Princeton, N.J.

A result interface 24 may also be incorporated into the signal processor 17. Results of the acoustic emission analysis provided by the micro processor 23 may be displayed and/or communicated in any manner known to persons of skill by the result interface 24. The result interface 24 may be as simple as an alarm indicating that a crack, leak, irregularity, crack nucleation, void, inclusion, etc. has been detected in the tubing 5 which exceeds the maximum allowable limit. The result interface 24 may also be much more complicated and provide complete reports in whatever form required.

According to one aspect of the invention, acoustic emission technology is used to determine the useful life and integrity of coiled tubing strings, including butt welds. Acoustic emission technology is a passive system that detects sound waves emitted by stressed or propagating cracks. Sensors are applied at one or more locations on the coil tubing as it is being plastically deformed over the gooseneck or reel. If cracks are present, they will be detected by the acoustic emission sensors. When the region around a crack tip exceeds a certain stress level (in some tubing it is about 60% of the tensile strength), a sound wave is emitted (frequency of interest usually about 100-300 KHz but may be broader even to the megahertz range). The sound wave is detected by the sensors which then convert it to an electrical impulse which is amplified and captured by a computer. Multiple sensors may be used to locate defects.

The stimulus required for acoustic emission signal generation occurs when the tubing 5 is plastically deformed as it is wound/unwound on/from the reel 2 or when it passes through the gooseneck 3 or injector head 4. Local plastic deformation may also occur in the tubing when the tubing undergoes internal or external pressure fluctuations. While macro plastic deformation usually does not occur during internal or external pressurings, internal or external hydrostatic pressure may deform regions of the tubing sufficiently to cause local plastic deformations. That is, if there is a defect (crack), then internal or external pressure on the entire pipe may case a plastic deformation at the crack tip exceeding the stress level. In this case, only the region of the defect (crack) plastically deforms to emit a signal. Where pressure is used to stimulate the acoustic emissions, a plurality of sensors placed near the defect area provides better signal acquisition.

When the tubing 5 experiences plastic deformation stresses, audible acoustic emission signals are generated by the tubing 5. Leaks in the tubing 5 may also generate an acoustic emission, usually well above the human audible range. The sensors 16 perceive the acoustic emissions as they are transmitted by the defects through the tubing 5. Because the amplitude of the acoustic energy propagating from the defect decreases as a function of distance from the defect (signal attenuation), the location of the leak may be identified. Knowledge of the attenuation characteristics of the tubing 5 allows one to use observed acoustic emissions at several locations along the tubing to identify the location of the defect. In coiled tubing 5, attenuation may be impacted by the type of material, the tubing wall thickness, supporting structural members such as the reel 2, the rollers 10, and the track 10, and any surface coatings applied to the tubing.

Figure 3:
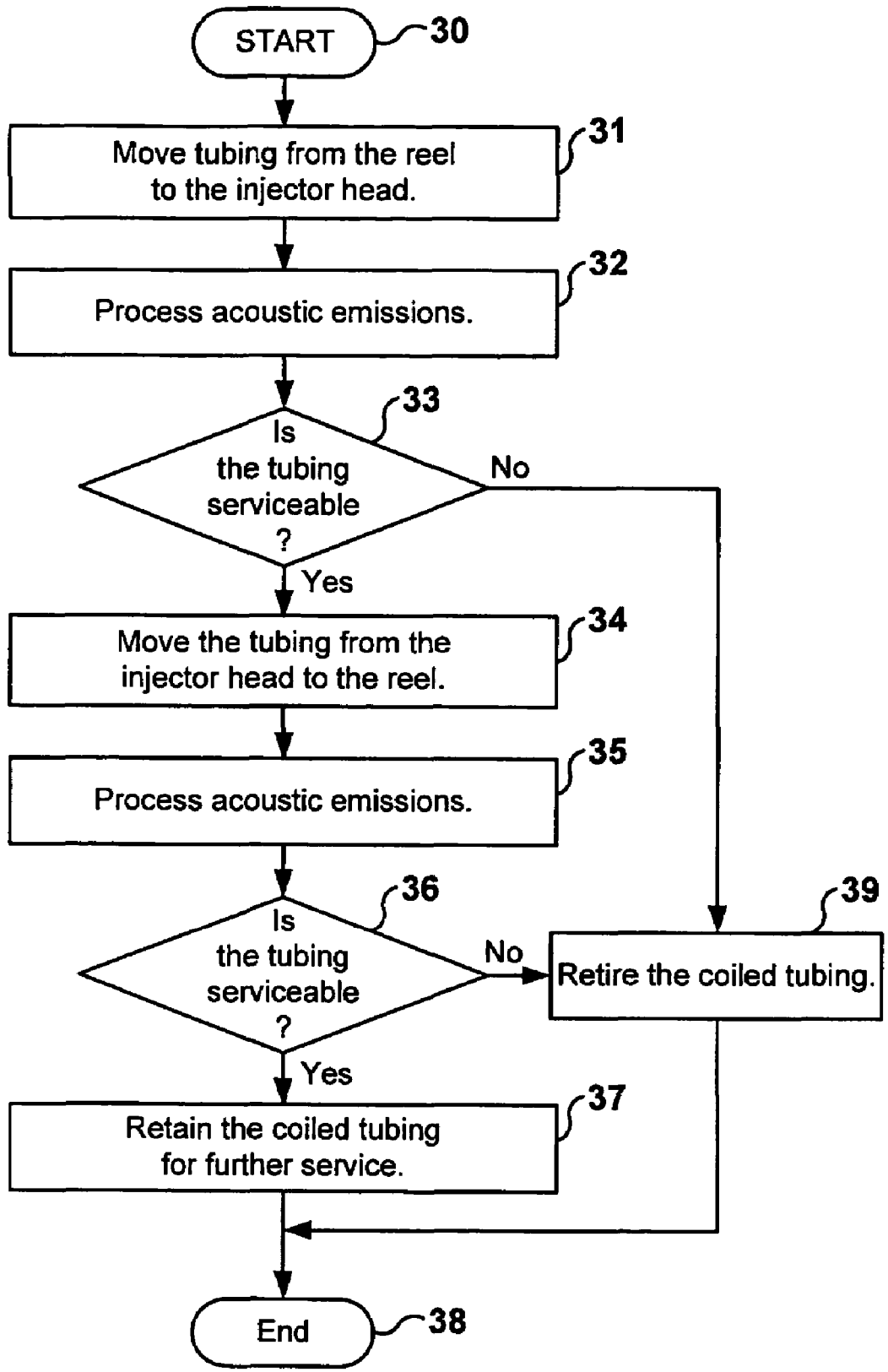
FIG. 3 is a block diagram illustrating a method for real-time testing coil tubing.

Referring to FIG. 3, a method for monitoring defects in coiled tubing is described. The process is started 30 and the coiled tubing 5 is moved 31 from the reel 2 to the injector head 4. As the coiled tubing 5 bends through the various support structures, the bending moments induce acoustic emissions from cracks, leaks, irregularities, crack nucleations, voids, inclusions, etc. The acoustic emissions are processed 32 by the signal processor 17 as described above. The result interface 24 indicates whether the tubing is serviceable 33. If the tubing 5 is no longer serviceable, the coil tubing 5 is retired 39 from service. If the tubing 5 is still serviceable, the tubing is fully injected in the well bore 13 to perform the intended downhole operation. Upon completion of the downhole operation, the coiled tubing 5 is moved 34 from the injector head 4 to the reel 2. As the coiled tubing 5 bends through the various support structures, the bending moments induce acoustic emissions from cracks, leaks, irregularities, crack nucleations, voids, inclusions, etc. The acoustic emissions are processed 35 by the signal processor 17 as described above. The result interface 24 indicates whether the tubing 5 is still serviceable 36. If the tubing 5 is no longer serviceable, the coil tubing 5 is retired 39 from service. If the tubing 5 is still serviceable, the coil tubing 5 is retained 37 for further operation on another well bore. The process is ended 38.

Figure 4:
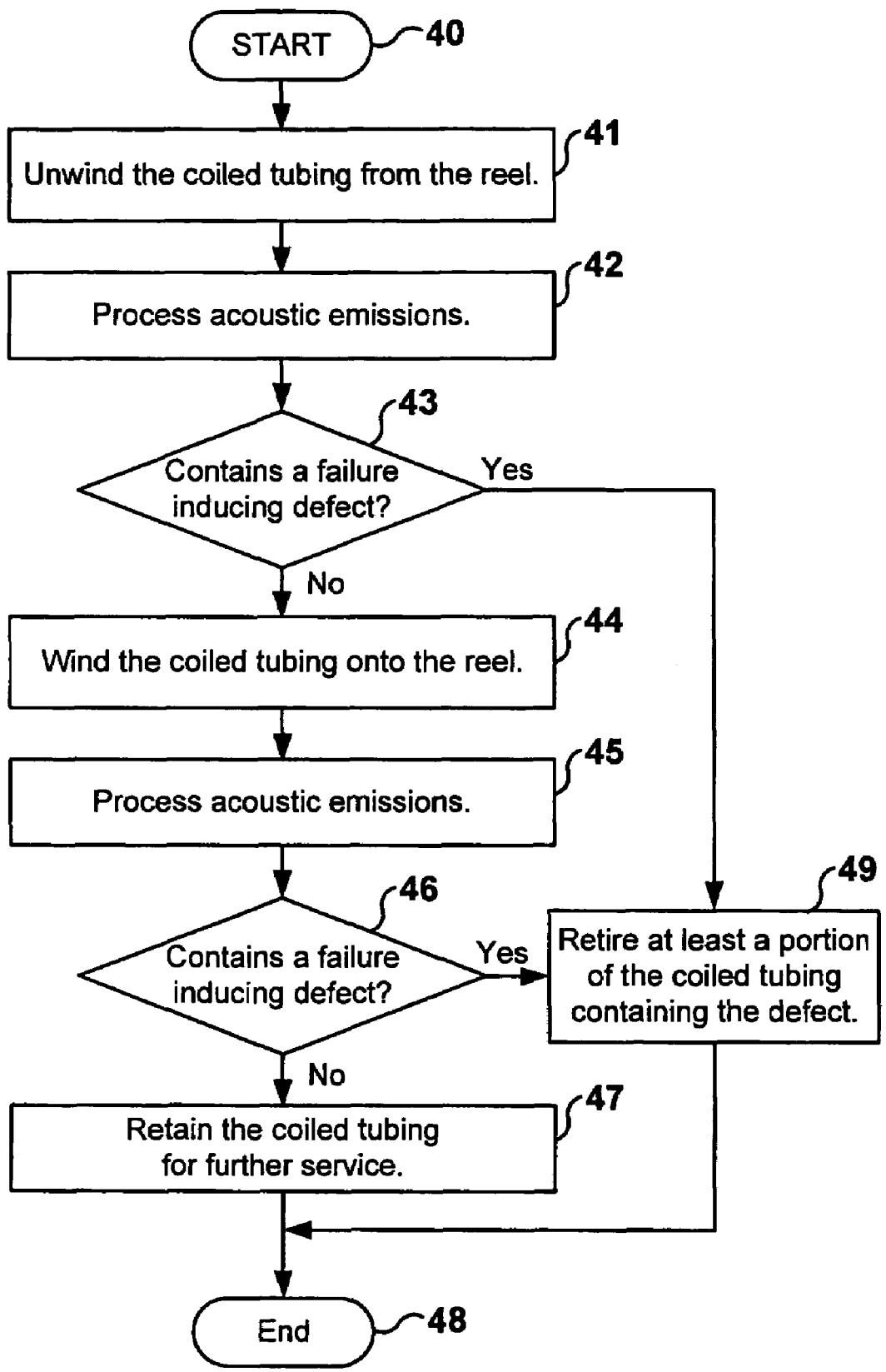
FIG. 4 is a block diagram illustrating an alternative method for real-time testing coil tubing.

Referring to FIG. 4, an alternative method for monitoring defects in coiled tubing is described. This method implements off-line acoustic emission testing of coiled tubing for use at a location remote from a well head, such as at a coiled tubing service center. The process is started 40 and the coiled tubing 5 is unwound 41 from the reel 2. In some embodiments, the coiled tubing also passes over a guide roller 12 or other device as it unwinds 41 from the reel 2. As the coiled tubing 5 bends off the reel 2, the bending moments induce acoustic emissions from cracks, leaks, irregularities, crack nucleations, voids, inclusions, etc. The acoustic emissions are processed 42 by the signal processor 17 as described above. The result interface 24 indicates whether a failure inducing defect has been identified 43. If the tubing 5 is found to contain a failure inducing defect, at least the portion of the coil tubing 5 containing the defect is retired 49 from service. In particular, a portion of the coiled tubing 5 may be cut out and replaced with another section of coiled tubing. If no failure inducing defects are identified, the coiled tubing 5 is wound 44 onto a reel 2. As the coiled tubing 5 bends onto the reel 2, the bending moments induce acoustic emissions from cracks, leaks, irregularities, crack nucleations, voids, inclusions, etc. The acoustic emissions are processed 45 by the signal processor 17 as described above. The result interface 24 indicates whether any failure inducing defects have been identified 46. If detected have been identified, at least a portion of the coil tubing 5 containing the defect is retired 49 from service and replaced with a new section or the two end portions of the tubing are joined together. If no defects are identified, the coil tubing 5 is retained 47 for further operations. The process is ended 48.

Therefore, the present invention is well adapted to carry out the objects and attain the ends and advantages mentioned as well as those that are inherent therein. While numerous changes may be made by those skilled in the art, such changes are encompassed within the spirit of this invention as defined by the appended claims.

What is claimed is:

1. A method of testing tubing plastically deformed by a tubing handling system, comprising:
   providing tubing for use in wells;
   plastically deforming the tubing by the tubing handling system;
   sensing with at least one sensor acoustic emission signals emitted by the tubing while plastically deforming; and
   processing the sensed acoustic emission signals.

2. The method of claim 1 wherein the tubing handling system comprises a reel, and the tubing plastically deforms when unwound from the reel.

3. The method of claim 1 wherein the tubing handling system comprises a reel, and the tubing plastically deforms when wound on the reel.

4. The method of claim 1 wherein the tubing handling system comprises a gooseneck, and the tubing plastically deforms when traveling over the gooseneck.

5. The method of claim 1 wherein the tubing handling system comprises an injector, and the tubing plastically deforms when pulled through the injector.

6. The method of claim 1 wherein the tubing handling system comprises a pump, and the tubing plastically deforms when a pressure differential exists between an inner diameter of the tubing and an exterior of the tubing.

7. The method of claim 1 wherein sensing the acoustic emission signals comprises contacting a rolling sensor with the tubing.

8. The method of claim 1 wherein processing the acoustic emission signals comprises amplifying the acoustic emission signals.

9. The method of claim 1 wherein processing the acoustic emission signals comprises filtering the acoustic emission signals.

10. The method of claim 1 wherein processing the acoustic emission signals comprises conducting knowledge-based software analysis on the acoustic emission signals.

11. The method of claim 1 further comprising generating an alarm when the processing of the acoustic emission signals indicates that a region of the tubing containing a defect has insufficient strength to support a certain stress level.

12. The method of claim 11 wherein the certain stress level is about 60% of the tensile strength of the tubing.

13. A method of testing tubing comprising:
    providing a tubing handling system comprising a reel, a gooseneck, and an injector;
    sensing, with at least one rolling sensor in direct contact with the tubing, acoustic emission signals emitted by the tubing while being plastically deformed by the tubing handling system;
    processing the sensed acoustic emission signals, wherein the processing comprises amplifying, filtering, and analyzing with knowledge-based software, the sensed acoustic emission signals; and
    generating an alarm when the processed acoustic emission signals indicates that a region of the tubing contains a defect having insufficient strength to support a stress level of at least about 60% of the tensile strength of the tubing.

14. A system for testing tubing, comprising:
    tubing for use in wells;
    a tubing handling system, wherein the tubing handling system plastically deforms the tubing;
    at least one acoustic emission sensor mounted on the tubing handling system and in direct contact with the tubing, wherein the at least one acoustic emission sensor senses acoustic emission signals emitted by the tubing while plastically deforming; and
    an acoustic emission signal processor in signal transmission communication with the at least one acoustic emission sensor.

15. The system of claim 14 wherein the tubing handling system comprises a reel, and the tubing plastically deforms as the tubing unwinds from the reel.

16. The system of claim 14 wherein the tubing handling system comprises a reel, and the tubing plastically deforms as the tubing winds on the reel.

17. The system of claim 14 wherein the tubing handling system comprises a gooseneck, and the tubing plastically deforms when traveling through the gooseneck.

18. The system of claim 14 wherein the tubing handling system comprises an injector, and the tubing plastically deforms when pulled through the injector.

19. The system of claim 14 wherein the tubing handling system comprises a pump, and the tubing plastically deforms when a pressure differential exists between an inner diameter of the tubing and an exterior of the tubing.

20. The system of claim 14 wherein the at least one acoustic emission sensor is a rolling sensor and is in rolling contact with the tubing.

21. The system of claim 14 wherein the acoustic emission signal processor comprises an amplifier.

22. The system of claim 14 wherein the acoustic emission signal processor comprises a filter.

23. The system of claim 14 wherein the acoustic emission signal processor comprises knowledge-based software.

24. The system of claim 14 further comprising an alarm, wherein the alarm is activated when the acoustic emission signal processor indicates that a region of the tubing containing a defect has insufficient strength to support a certain stress level.

25. The system of claim 24 wherein the certain stress level is about 60% of the tensile strength of the tubing.

26. A system for testing tubing, comprising:
    a tubing handling system, wherein the tubing handling system comprises a reel, a gooseneck, and an injector;
    at least one rolling acoustic emission sensor mounted on the tubing handling system and in direct contact with the tubing, wherein the at least one rolling acoustic emission sensor senses acoustic emission signals emitted by the tubing while the tubing handling system is plastically deforming the tubing;

an acoustic emission signal processor in signal conmmnication with the at least one acoustic emission sensor; and an alarm in signal communication with the acoustic emission signal processor, wherein the alarm is activated when the acoustic emission signal processor indicates that a region of the tubing containing a defect has insufficient strength to support a certain stress level.

27. The system of claim 26 wherein the certain stress level is about 60% of the tensile strength of the tubing.

28. The system of claims 26 wherein the acoustic emission signal processor comprises an amplifier, a filter, and knowledge-based software.

* * * * *